(12) United States Patent
Meadows

(10) Patent No.: US 6,589,205 B1
(45) Date of Patent: Jul. 8, 2003

(54) EXTERNALLY-CONTROLLABLE CONSTANT-FLOW MEDICATION DELIVERY SYSTEM

(75) Inventor: Paul M. Meadows, La Crescenta, CA (US)

(73) Assignee: Advanced Bionica Corporation, Sylmar, CA (US)

( * ) Notice: Subject to any disclaimer, the term of this patent is extended or adjusted under 35 U.S.C. 154(b) by 191 days.

(21) Appl. No.: 09/715,280

(22) Filed: Nov. 16, 2000

Related U.S. Application Data

(60) Provisional application No. 60/172,165, filed on Dec. 17, 1999.

(51) Int. Cl.[7] ............................................. A61M 31/00
(52) U.S. Cl. ...................... 604/67; 604/890.1; 604/246; 604/288.01
(58) Field of Search .......................... 604/890.1, 891.1, 604/502, 131, 246–256, 288.01, 65–67

(56) References Cited

U.S. PATENT DOCUMENTS

| | | | |
|---|---|---|---|
| 4,299,220 A | 11/1981 | Dorman | 128/260 |
| 4,360,019 A * | 11/1982 | Portner et al. | 604/131 |
| 4,373,527 A * | 2/1983 | Fischell | 128/903 |
| 4,411,651 A * | 10/1983 | Schulman | 417/63 |
| 4,443,218 A * | 4/1984 | DeCant et al. | 128/DIG. 12 |
| 4,447,224 A * | 5/1984 | DeCant et al. | 128/DIG. 12 |
| 4,487,603 A * | 12/1984 | Harris | 128/DIG. 12 |
| 4,561,443 A * | 12/1985 | Hogrefe et al. | 128/903 |
| 4,679,560 A | 7/1987 | Galbraith | 128/419 |
| 4,714,462 A * | 12/1987 | DiDomenico | 604/141 |
| 4,718,893 A * | 1/1988 | Dorman et al. | 128/DIG. 12 |
| 4,731,051 A * | 3/1988 | Fischell | 604/502 |
| 4,871,351 A * | 10/1989 | Feingold | 128/DIG. 12 |
| 5,009,251 A | 4/1991 | Pike et al. | 137/601 |
| 5,067,943 A * | 11/1991 | Burke | 604/141 |
| 5,088,983 A * | 2/1992 | Burke | 604/141 |
| 5,328,460 A * | 7/1994 | Lord et al. | 128/DIG. 12 |
| 5,382,236 A | 1/1995 | Otto et al. | 604/141 |
| 5,514,103 A | 5/1996 | Srisathapat et al. | 604/141 |
| 5,607,418 A | 3/1997 | Arzbaecher | 604/891 |
| 5,722,957 A | 3/1998 | Steinbach | 604/141 |
| 5,785,688 A | 7/1998 | Joshi et al. | 604/141 |
| 5,810,015 A * | 9/1998 | Flaherty | 128/897 |
| 5,814,019 A | 9/1998 | Steinbach et al. | 604/131 |
| 5,836,915 A | 11/1998 | Steinbach et al. | 604/131 |
| 5,876,425 A | 3/1999 | Gord et al. | 607/56 |
| 5,891,097 A | 4/1999 | Saito et al. | 604/141 |
| 5,924,848 A * | 7/1999 | Izraelev | 415/900 |
| 5,938,412 A * | 8/1999 | Izraelev | 415/206 |
| 5,948,006 A * | 9/1999 | Mann | 128/903 |
| 5,957,890 A | 9/1999 | Mann et al. | 604/131 |
| 5,993,414 A * | 11/1999 | Haller | 604/131 |
| 6,048,328 A * | 4/2000 | Haller et al. | 604/131 |
| 6,203,523 B1 * | 3/2001 | Haller et al. | 604/131 |
| 6,206,659 B1 * | 3/2001 | Izraelev | 415/900 |
| 6,241,704 B1 * | 6/2001 | Peterson et al. | 604/31 |
| 6,275,737 B1 * | 8/2001 | Mann | 607/61 |
| 6,283,944 B1 * | 9/2001 | McMullen et al. | 604/151 |
| 6,358,239 B1 * | 3/2002 | Rake et al. | 604/890.1 |
| 6,464,687 B1 * | 10/2002 | Ishikawa et al. | 604/891.1 |
| 2002/0013545 A1 * | 1/2002 | Soltanpour et al. | 604/9 |

* cited by examiner

*Primary Examiner*—Ira S. Lazarus
*Assistant Examiner*—Andrea M. Ragonese
(74) *Attorney, Agent, or Firm*—Kenneth L. Green; Laura Haburay Bishop; Bryant R. Gold

(57) ABSTRACT

A medication infusion system includes an implantable device and an external control device. The implantable device includes a constant flow pump and a flow rate that may be altered by commands received from the external control device. Power to execute the commands is also provided to the passive pump from the external control device. The external control device sends a command only when a flow rate change is to be made, or when status information is required. In one embodiment, the flow rate provided by the passive pump is controlled by a flow regulator, where the flow rate is changed by changing the restriction of a passage between regulator chambers.

17 Claims, 4 Drawing Sheets

EXTERNALLY-CONTROLLABLE CONSTANT-FLOW MEDICATION DELIVERY SYSTEM

The present application claims the benefit of U.S. Provisional Application Ser. No. 60/172,165, filed Dec. 17, 1999, which application is incorporated herein by reference.

BACKGROUND OF THE INVENTION

The present invention relates to the external control of the flow rate of a constant flow fluid delivery device and more particularly to the external control of an implantable constant flow medication infusion pump.

There are two basic types of implantable pumps: constant flow pumps and programmable rate pumps. In the constant flow (or passive) pump, the flow rate is fixed, so in order to control the amount of medication delivered, the clinician must set the concentration of the medication taking into account the fixed flow rate of the pump. Patients needing changes to their medication delivery rate must visit their physician, who removes the remaining medication in the reservoir, and replaces it with a medication at a different concentration. U.S. Pat. No. 5,836,915 issued Nov. 17, 1998 for "Implantable Infusion Pump" describes such a constant flow pump that comprises two chambers divided by a flexible membrane. The pump described in the '915 patent includes a first chamber containing the medication to be pumped, and a second chamber containing a motive substance. The motive substance creates pressure in the second chamber that is transferred to the first chamber by the membrane. The motive substance is selected so that the pressure remains constant, and therefore the rate of the resulting medication flow remains constant also.

Alternatively, programmable pumps can provide variable flow rates. Programable pumps may deliver the medication either by solenoid pump or by peristaltic pump. In the solenoid pump, the flow rate can be controlled by changing the stroke rate of the pump. In the peristaltic pump, the flow rate can be controlled by changing the roller velocity. Disadvantageously, both types of programmable pumps generally require a battery and sophisticated controllers to enable their operation and control.

A pump could be made utilizing a cable passing through the skin to control the pumping rate. However, a cable connection through the skin of the patient interferes with the freedom of movement of the patient, and represents a possible source of infection.

Therefore, there is a need for a constant flow pump with a means for varying its flow rate, that overcomes the limitations of the existing constant flow pumps without the complexity of the existing programable pumps, and avoids using a control cable that passes through the skin.

SUMMARY OF THE INVENTION

The present invention addresses the above and other needs by providing an externally controllable constant flow medication delivery system that retains the simple robust features of a constant flow pump, while providing a capability to adjust flow rates. The system utilizes an external control device and an implantable pump. The implantable pump includes a constant flow pump and a controllable flow regulator. Flow rate commands are provided to the implantable pump from the external control device via an RF link. An actuator is mechanically connected to the flow regulator, and mechanically adjusts the flow regulator each time a new flow rate is commanded. The power required by the actuator to execute flow rate changes is also provided via the same RF link.

It is a feature of the present invention to provide an implantable pump with a flow rate that may be adjusted by an external device. The capability to easily alter the medication flow rate allows a physician to maintain a single or small inventory of medication concentrations for refilling the implantable pump, and alleviates the need to remove medication of one concentration and refill with medication of another concentration when a change in delivery rate is required.

It is another feature of the present invention to provide control signals over an RF link. Such RF link avoids the use of a cable through the skin and the discomfort and risk of infection that may result from a cable through the skin.

It is yet another feature of the present invention to provide an implantable pump with the simplicity of a constant flow rate pump, simple electronics, and no requirement for a battery. Advantageously, such a simple pump provides both durability and reduced cost.

In accordance with another aspect of the present invention, the only power required by the implantable pump is the power needed to change the flow rate. Advantageously, that power is provided by an external control device over an RF link. Therefore, the implantable pump requires no internal power source.

It is a further feature of the present invention to encode a unique serial number on the transmitted flow rate commands. This unique serial number functions as a password so that only intentional flow rate changes are executed by the implantable pump.

It is an additional feature of the present invention to provide back telemetry from an implantable pump to an external control device. The back telemetry provides a means through which data may be sent to the external control device. Such data may include system status information, e.g., confirmation that the flow rate command had been executed, pressure, present flow rate, or other instantaneous measurements.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
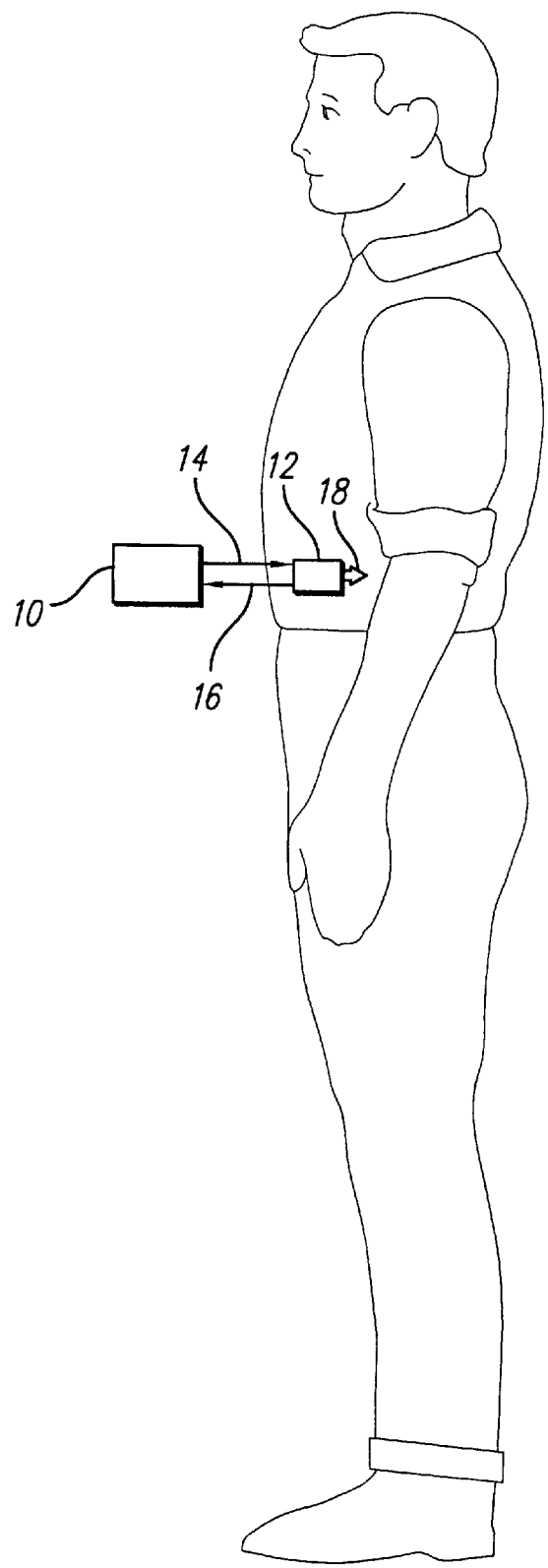
FIG. 1 depicts a medication infusion system implanted in a patient.

An externally controllable constant flow medication delivery system, in accordance with the present invention, is shown in FIG. 1. The medication delivery system comprises an external control device 10 and an implantable pump 12. The external control device 10 uses forward telemetry 14 to provide control signals and power signals to the implantable pump 12. The implantable pump 12 utilizes the power contained in the power signals to make changes to its flow rate according to the control information contained in the control signals. The implantable pump 12 uses back telemetry 16 to provide status information to the external control device 10. Further, the implantable pump 12 provides a medication flow 18 in response to the commands received from the external control device 10 over the forward telemetry 14.

Figure 2:
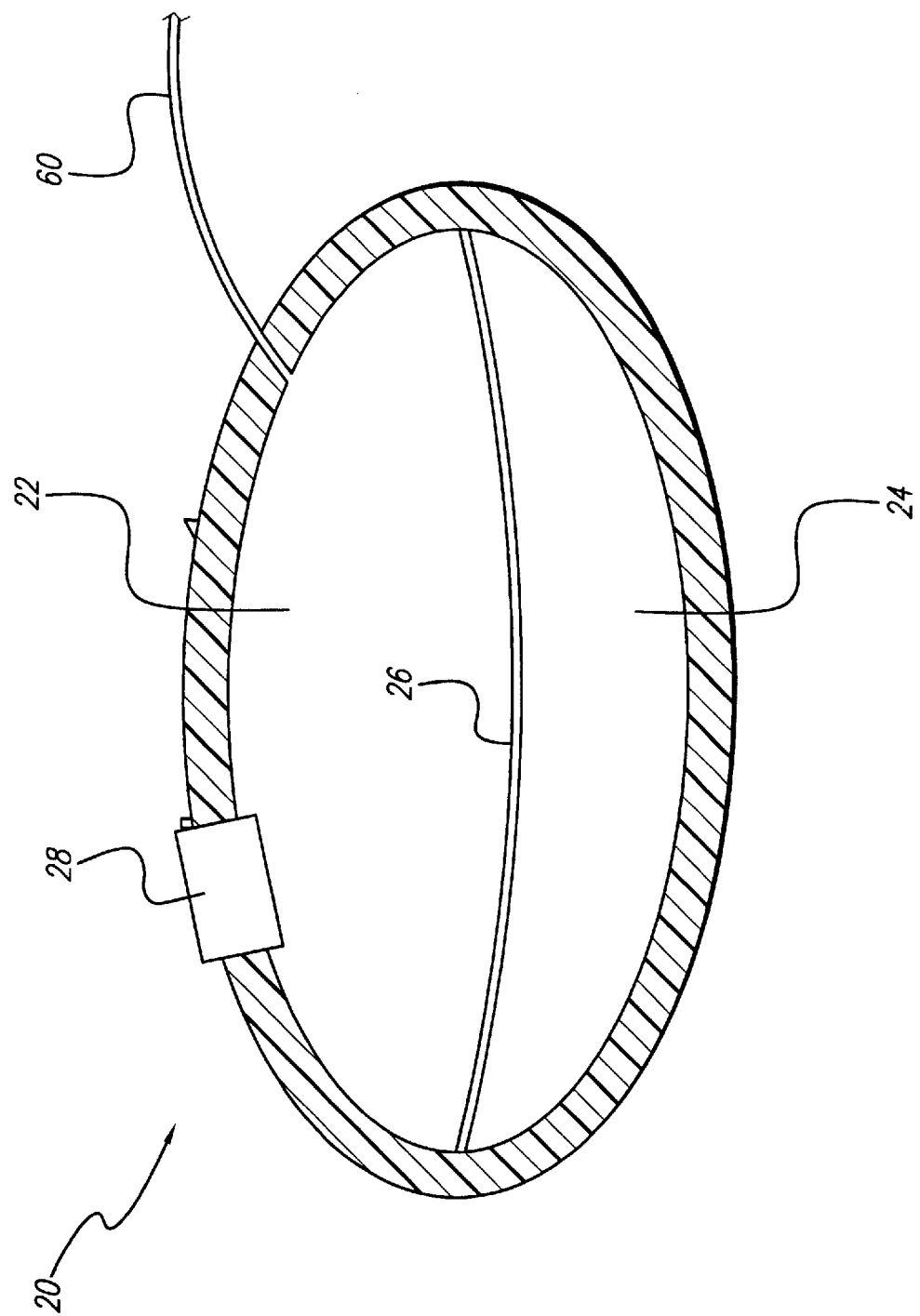
FIG. 2 depicts an implantable constant flow rate pump.

The present invention may be exercised using any of a variety of existing constant flow pumps. Turning to FIG. 2, a sketch of a vertical section through a typical passive flow pump 20 is shown. The passive pump 20 comprises a medication reservoir 22 that contains the medication to be pumped, a pressure chamber 24 containing a motive substance, a gas impermeable membrane 26 separating the motive substance from the medication, and a refill aperture 28 allowing medication to be added to the medication reservoir 22.

Constant flow pumps are well known in the art. U.S. Pat. No. 5,836,915 issued Nov. 17, 1998 for "Implantable Infusion Pump" describes such a constant flow pump. Various other constant flow pumps are known in the art and are described, e.g., in: U.S. Pat. No. 5,957,890 issued Sep. 28, 1999 for "Constant flow medication infusion pump," U.S. Pat. No. 5,814,019 issued Sep. 29, 1998 for "Implantable infusion pump," U.S. Pat. No. 5,607,418 issued Mar. 4, 1997 for "Implantable drug delivery apparatus," and U.S. Pat. No. 5,382,236 issued Jan. 17, 1993 for "Implantable infusion pump." The '915, '890, '019, and '418 patents are incorporated herein by reference.

Known implantable constant flow pumps operate at a single flow rate. The amount of medication provided to the patient is determined by the pump selected and the concentration of the medication. If there is a need to change the dosage, the remaining medication must be removed from the pump, and the medication reservoir of the pump refilled with medication of a new concentration.

Figure 3:
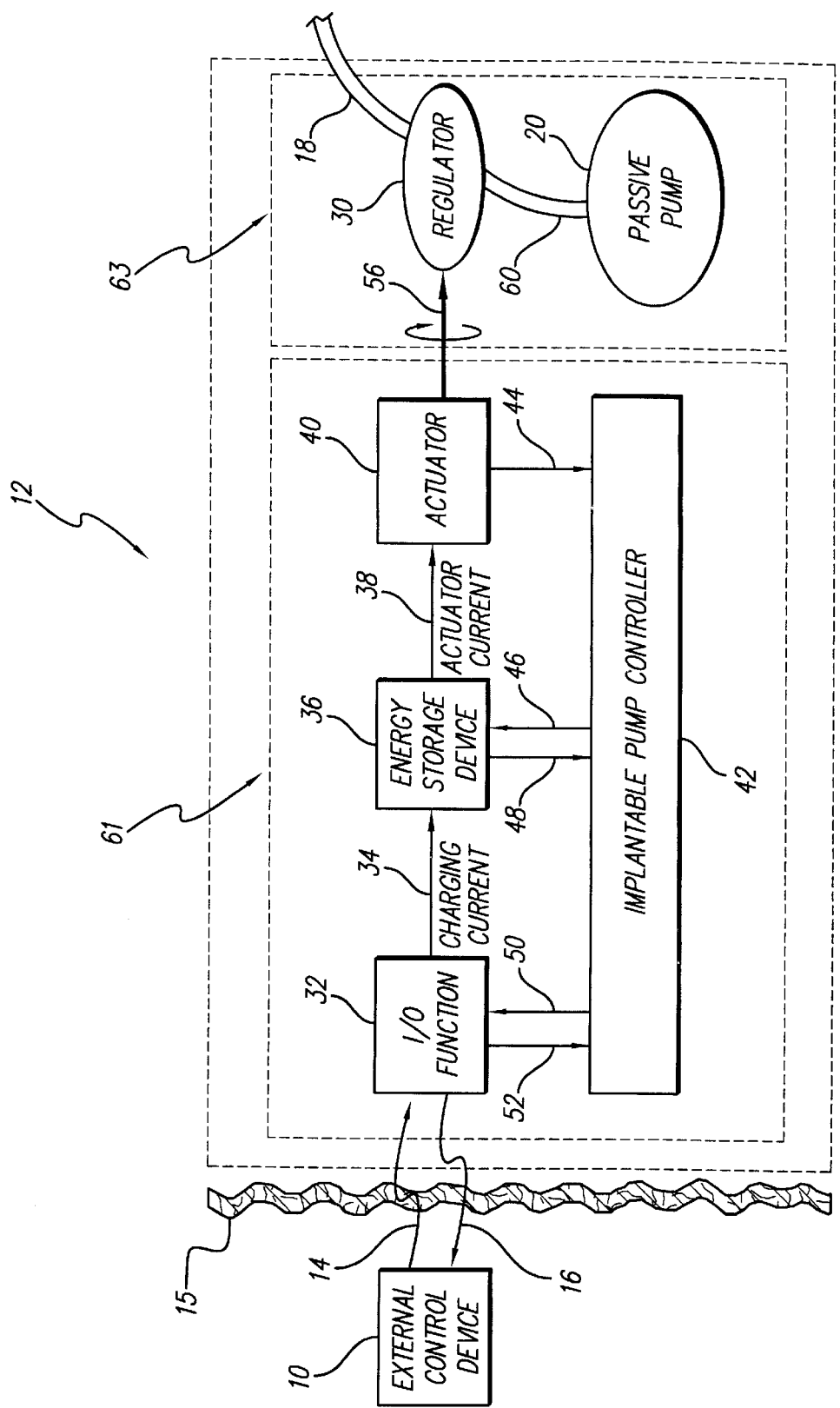
FIG. 3 shows a high level functional block diagram of a controllable constant flow rate pump.

A high level functional flow of the externally controllable constant flow medication delivery system is shown in FIG. 3. The implantable pump 12 comprises a control section 61 and a mechanical section 63. The forward telemetry 14 provides a command and power signal from the external control device 10 through skin 15, and to an I/O function 32 of the implantable pump 12. The I/O function 32 filters the forward telemetry 14 and provides a charging current 34 to an energy storage device 36, preferably a capacitor, and a control signal 50 to an implantable pump controller 42.

A charge level 46 of the energy storage device 36 is provided to the implantable pump controller 42. When the charge level 46 reaches the level required to execute the command, the implantable pump controller 42 sends an execute command 48 signal to energy storage device 36 and an actuator current 38 is provided by the energy storage device 36 to an actuator 40. The actuator 40 is a mechanical device that converts the current into a mechanical actuation 56 used to change a flow rate through a regulator 30 and thus regulate a pump output 60 from the passive pump 20 to yield the medication flow 18.

The actuator 40 sends actuator data 44 to the implantable pump controller 42 to verify that the command has been executed. The implantable pump controller 42 sends a status message 52 to the I/O function 32, which status message 52 contains the verification that the command has been successfully executed, along with other status information. The I/O function 32 provides the status information to the external control device over the back telemetry 16.

The capability to determine in advance that sufficient energy is stored to complete a commanded change, before the change is initiated, is an important safety feature. Such safety feature prevents partially-executed commands from occurring, which partially-executed commands might otherwise cause the implantable pump 12 to operate improperly.

Thus, the present invention provides the capability to vary the flow rate, without the added complexity of a programmable pump, by adjusting the characteristics of the flow regulator 30. When there is a requirement to change the flow rate of the flow regulator 30, the external control device 10 is positioned adjacent to the implant location of the implantable pump 12. Using the forward telemetry 14, or another suitable link, the external control device 10 provides both power and control information to the implantable pump 12. The control signal may be provided through modulation of an RF power signal that is inductively linked with an implantable pump. A similar use of forward telemetry in cochlear stimulation systems is described in U.S. Pat. No. 5,876,425 issued Mar. 2, 1999 for "Power control loop for implantable tissue stimulator," which '425 patent is incorporated herein by reference. The '425 patent describes RF forward telemetry used to provide power and control to an Implantable Cochlear Stimulator. The telemetry of the power required to change the flow rate of the flow regulator 30, advantageously eliminates the requirement for a battery within the implantable pump.

U.S. Pat. No. 4,679,560 issued Jul. 14, 1987 for "Wide band inductive transdermal power and data link," describes an inductive link where the values of the capacitor and coil inductance are selected to provide a stagger-tuned link. As a result of desensitizing the link to the coupling, the coils can be misaligned in any manner with little effect on the output. This feature is advantageous in some applications of the present invention because the external control device 10 is not permanently attached, and the orientation of the external control device 10 to the implantable pump 12 may not always be precise. The '560 patent is likewise incorporated herein by reference. Those skilled in the art will recognize that other methods of providing power to an implantable device are known and applicable, and that such other methods may be used to practice the present invention.

Further, various methods of fixing or setting the flow rates of constant flow pumps are also known in the art. U.S. Pat. No. 4,299,220 issued Nov. 10, 1981 for "Implantable Drug Infusion Regulator," for example, describes a method of using a pressure regulator to regulate the flow of an implantable pump. The '220 patent is incorporated herein by reference. The particular approach used to control the flow rate in the '220 patent advantageously provides a flow rate control which is tolerant to changes in temperature and ambient pressure. The '220 patent further describes the use of capillary restrictors of various restrictions as components of the flow regulator, which components may be used to determine the flow rate.

Figure 4:
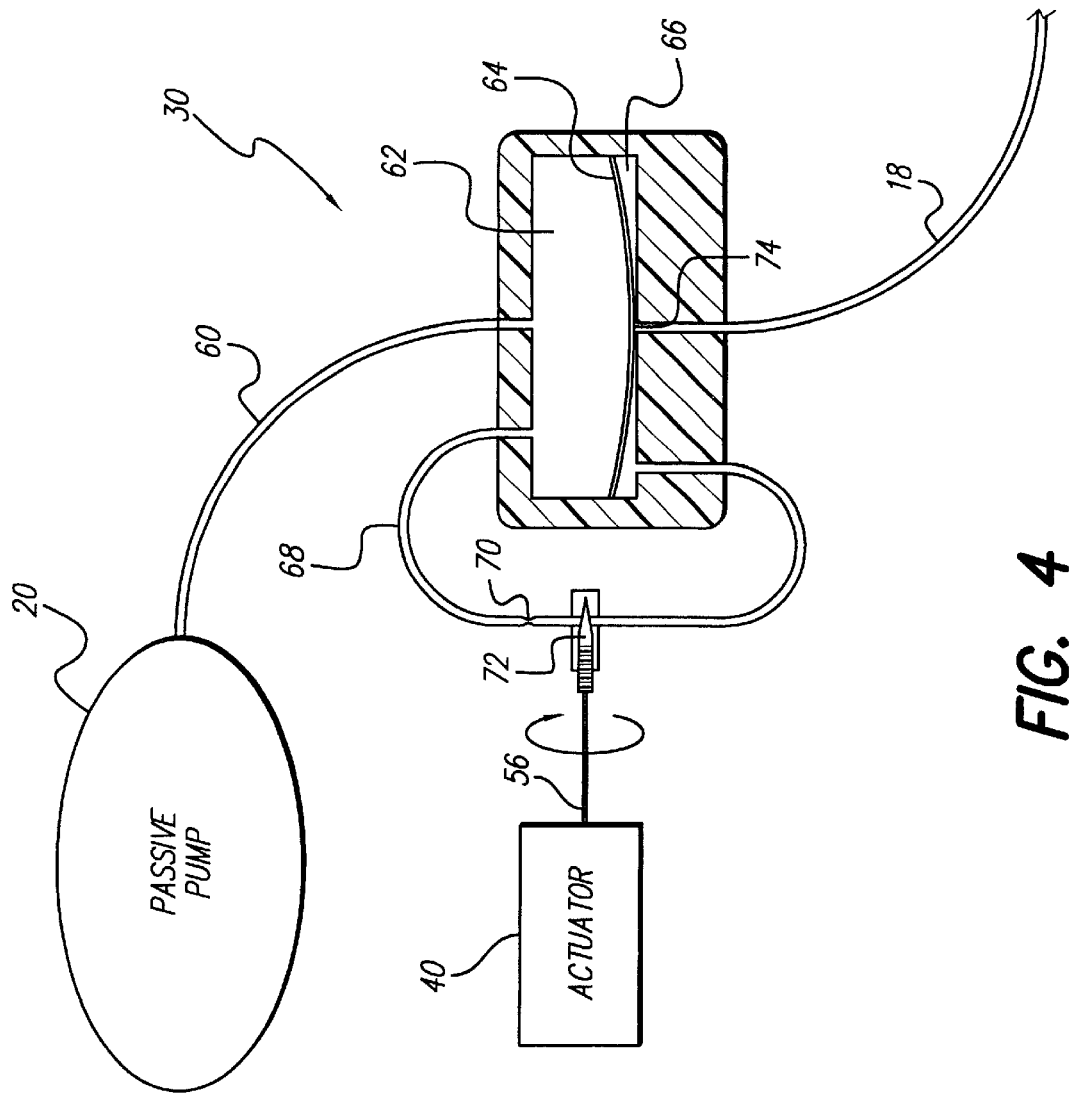
FIG. 4 shows a high level diagram of the mechanical parts of a controllable constant flow rate pump.

In one embodiment of the present invention a flow regulator 30 of the type described in the '220 patent, is modified so that the restriction provided by a capillary restrictor may be mechanically altered, thus altering the flow rate. As shown in FIG. 4, the passive pump 20 provides the pump output 60 to the regulator 30. The pump output 60 enters a pressure sensing chamber 62 and provides downward pressure on a regulator diaphragm 64. A restricted flow line 68 connects the pressure sensing chamber 62 with a valving chamber 66, which valving chamber 66 is on the side of the diaphragm 64 opposite the pressure sensing chamber 62. Restrictions in the restricted flow line 68 result in a pressure gradient between the pressure sensing chamber 62 and the valving chamber 66, and the pressure gradient results in the diaphragm 64 being pressed down against the outlet valve 74, thus restricting the medication flow 18 out of the flow regulator 30. The result is that the medication flow 18 remains constant over a range of conditions. A fixed restriction 70 in the restricted flow line 68 may be augmented by a needle valve 72. When a command is received to change the flow rate, the needle valve 72 is turned a fixed number of degrees by the actuation 56 provided by the actuator 40, thus changing the total restriction and therefore the medication flow 18. Advantageously, power is only required while the chance is being made. Once the power is removed, the flow rate will remain constant until another command is issued.

In a second embodiment of the present invention, a flow regulator as described in U.S. Pat. No. 5,009,251 issued Apr. 23, 1991 for "Fluid Flow Control," is used. The '251 patent is incorporated herein by reference. The '251 patent describes a flow regulator comprising a plurality of unique flow restriction passageways, each passageway having a unique degree of restriction. A rotatable cam and a plurality of valves are provided wherein the cam depresses (i.e. closes) all but one valve, and the position of the cam determines which valve is open. A simple solenoid and ratchet mechanism is adapted to turn the cam and provide different flow rates. As in the case of the needle valve above, power is required only when a change is made. Additionally, the unique position of the cam is available for back telemetry to provide an accurate indicator of the present flow rate.

Other methods of controlling the flow rate from a constant flow pump may also be used. Such methods may involve modification of known flow rate control techniques, existing flow rate control techniques without modification, or yet to be developed flow rate altering techniques.

Another feature of the invention is the use of an individual code for each implantable pump 12. Such individual code functions as a password and must be included in a flow rate change command in order for the command to be executed, thus providing a secure setting of delivery rates. Each implantable pump 12 is assigned a unique code, e.g., a serial number. When a new flow rate is commanded, the command signal includes the code of the target pump. The circuitry within the pump only executes the command if the pump recognizes the correct code. When an incorrect code is received, the pump transmits an error message using the back telemetry 16. This feature of the invention also provides a method of limiting changes depending upon who requests the change. For example, a patient with a first code may be allowed or permitted to make a limited range of changes; whereas a physician with a second code may be permitted to make changes over a wider range. Further, this feature advantageously prevents anomalous commands from being executed.

In addition to providing a control signal and the power to execute the command, the present invention also provides, through the back telemetry 16, for the transmission of status information from the implantable pump 12 to the external control device 10. The '425 patent described above and incorporated herein by reference, describes a suitable back telemetry system that may be used for this purpose.

Similarly, the back telemetry 16 may also be used to provide various status or other data from the implantable pump 12 to the external control device 10. Such status may include, e.g., an echo of a new flow rate command, confirmation that a command has been successfully completed, current flow rate, remaining medication, pressure, problem codes, etc.

Significantly, there is no requirement for a power storage device in the implantable pump 12, in order to deliver medication. However, when a power storage device is not provided in the implantable pump 12, there is no capability to monitor and record the pump's performance for later reporting. Hence, in a preferred embodiment the implantable pump includes some type of power storage means for monitoring and recording. Any type of power storage means would suffice.

It is further noted that some measurements might require sensors to make the measurements before they can be transmitted to the external control device 10. In each particular application, the cost of adding sensors to the implantable pump may be traded off against the value of the measurements.

By way of example, it is noted that refilling the medication reservoir 22 is a medical procedure requiring a needle to be inserted through the patent's skin and through the refill aperture 28, and the medication reservoir 22 may only be refilled a finite number of times before the refill aperture 28 loses its ability to seal the medication reservoir 22. If the remaining medication can be accurately reported, the intervals between refilling may be extended. In some cases this may provide sufficient value to warrant including a capability within the implantable pump to measure the amount of medication remaining in the medication reservoir 22. Advantageously, in some embodiments of the invention, an external control device with the limited capability of retrieving pump status information, may be provided to the patient, thus permitting frequent and convenient monitoring of the status of the implantable pump 12.

While the primary application of the present invention is directed to an implantable pump 12, it should also be noted that the invention may also be practiced with an external pump. In situations where an external pump is providing medication, and a secure method of changing flow rates is desired, the present invention may be used. For example, in a health care environment where only certain individuals are authorized to make changes to medication rates, the present invention may be used. That is, the implantable pump 12 would be replaced by an external pump, which could be functionally similar to the constant flow pump 20 described herein. The external pump would provide medication at a designated rate until an external control device 10 is held adjacent to the external pump, and a new flow rate command is transmitted along with the power required to make the change. At the same time, status information may be transmitted from the external pump to the external control device 10. In the absence of the external control device 10, and the correct code, the flow rate would remain unchanged.

While the invention herein disclosed has been described by means of specific embodiments and applications thereof, numerous modifications and variations could be made thereto by those skilled in the art without departing from the scope of the invention set forth in the claims.

What is claimed is:

1. A pump comprising:
    a passive pump adapted to provide a flow of medication to a patient;
    a regulator adapted to regulate the flow of the medication from the passive pump to the patient to obtain a constant flow rate, wherein the regulator includes a pressure sensing chamber, a valving chamber, and a flow line between the pressure sensing chamber and the valving chamber;

an actuator adapted to adjust the regulator to change the constant flow rate to a new constant flow rate, wherein the actuator is adapted to respond to flow rate control commands received over a communications link; and a needle valve connected to the actuator and positioned to mechanically alter the flow rate through the flow line of the regulator, wherein the needle valve is turned by the actuator a number of degrees to mechanically alter the flow rate through the flow line to a new flow rate within a range of possible new flow rates corresponding to the number of degrees the needle valve is turned by the actuator.

2. A pump comprising:

a passive pump adapted to provide a flow of medication to a patient;

a regulator adapted to regulate the flow of the medication from the passive pump to the patient to obtain a constant flow rate, wherein the regulator includes a pressure sensing chamber, a valving chamber, and a flow line between the pressure sensing chamber and the valving chamber, wherein the flow line includes a restriction;

an actuator adapted to adjust the regulator to change the constant flow rate to a new constant flow rate, wherein the actuator is adapted to respond to flow rate control commands received over a communications link, said actuator including means for varying the restriction in the flow line, wherein the means for varying the restriction comprises a needle valve in the restricted flow line, wherein the actuator turns the needle valve a number of degrees to mechanically alter the flow rate to a new flow rate within a range of possible new flow rates corresponding to the number of degrees the needle valve is turned by the actuator.

3. The pump of claim 1 wherein said communications link is adapted to provide back telemetry of status information.

4. The pump of claim 1 wherein said communications link is an RF link.

5. The pump of claim 1, wherein the flow rate control command and a power signal for providing power for executing the flow rate control command are received over the communications link.

6. The pump of claim 1 wherein the pump is an implantable pump, and wherein the communications link is a transcutaneous RF link.

7. The pump of claim 1 wherein the pump includes a unique code, wherein the pump responds to the flow rate control commands which include the unique code, and ignores the flow rate control commands not including the unique code.

8. The pump of claim 1 wherein the pump includes at least two codes and at least two ranges of responses, wherein each of the at least two codes is matched to one of the at least two ranges of responses, and wherein the response of the pump to the flow rate control commands is limited to the range of responses that is matched to the code contained in the flow rate control commands.

9. A controllable constant flow medication delivery system comprising:

a control device; and a pump comprising:

a passive pump;

a regulator including a flow line between a pressure sensing chamber and a valving chamber, wherein the regulator is adapted to regulate a constant flow rate of medication from the passive pump to a patient;

a needle valve positioned in the flow line of the regulator; and an actuator adapted to adjust the regulator to control the constant flow rate by turning said needle valve a number of degrees to set a new constant flow rate within a range of possible new constant flow rates corresponding to the number of degrees the needle valve is turned by the actuator;

wherein said control device provides a flow rate control command over a communications link to the actuator, and the actuator adjusts the regulator in response to the flow rate control command to change the constant flow rate to a new constant flow rate.

10. The system of claim 9 wherein said regulator provides a constant flow rate until the flow rate is changed by said actuator.

11. The system of claim 9, wherein the pump includes a unique code and wherein the pump responds to the flow rate control command only if the flow rate control command includes the unique code.

12. The system of claim 9, wherein said pump is adapted to provide status information to the control device over the communications link using back telemetry.

13. The system of claim 9 wherein the control device is adapted to reside external to the body of the patient, and wherein the pump is adapted to be implanted into the body, and wherein the control device is adapted to transmit control signals through skin to the pump.

14. The system of claim 9 wherein the communications link is an RF link.

15. The system of claim 14 wherein the RF link provides a power signal to the pump, wherein the power signal is used to provide power to the actuator.

16. The system of claim 9, wherein said pump is adapted to provide status information including an amount of medication remaining in the pump, to the control device over the communications link using back telemetry.

17. The pump of claim 9 wherein the pump includes at least two codes and at least two ranges of responses, wherein each of the at least two codes is matched to one of the at least two ranges of responses, and wherein the response of the pump to the flow rate control commands is limited to the range of responses that is matched to the code contained in the flow rate control commands.

* * * * *